US006251066B1

(12) United States Patent
Pack

(10) Patent No.: US 6,251,066 B1
(45) Date of Patent: Jun. 26, 2001

(54) THRUSTING ROD

(76) Inventor: Juergen Pack, Hermann-Schuster-Strasse 70, D-65510 Hünstetten-Wallbach (DE)

( * ) Notice: Subject to any disclaimer, the term of this patent is extended or adjusted under 35 U.S.C. 154(b) by 0 days.

(21) Appl. No.: 09/369,662

(22) Filed: Aug. 5, 1999

(30) Foreign Application Priority Data

Apr. 19, 1999 (DE) .......................................... 299 06 964 U

(51) Int. Cl.[7] .......................................... A61F 5/00
(52) U.S. Cl. .......................................... 600/38; 601/97
(58) Field of Search .......................... 600/38–42; 601/97, 601/105, 84

(56) References Cited

U.S. PATENT DOCUMENTS 4,722,327 * 2/1988 Harvey .................................. 601/97
4,790,296 * 12/1988 Segal .................................. 601/97

* cited by examiner

*Primary Examiner*—John P. Lacyk

(57) ABSTRACT

An artificial penis has a cylinder having a cylinder wall enclosing a hollow, a front wall with a first opening and a rear wall with a second opening. A piston rod is guided within the hollow. The piston rod has an initial position in which a first cylinder space is at a maximum and a second cylinder space is at a minimum and an extended position in which the first cylinder space is at a minimum and the second cylinder space at a maximum. A pump supplies a fluid under pressure to move the piston rod in an extending direction. An enclosure having an outer shape of a penis encloses the cylinder and the end of the piston rod. The enclosure has an initial position when the pump is released and an extended position when the pump is actuated.

9 Claims, 1 Drawing Sheet

THRUSTING ROD

The invention relates to a thrust rod in the form of a penis.

Numerous erotic articles in the form of a penis are known. The inventor has taken the trouble to add to these a further variant such that the device is capable of being used in a manner which was unknown heretofore.

The given object is attained on the basis of the features of the claim, and is developed and further elaborated by the further features of the dependent claims.

The invention is described with reference to the accompanying drawing.

Figure 1:
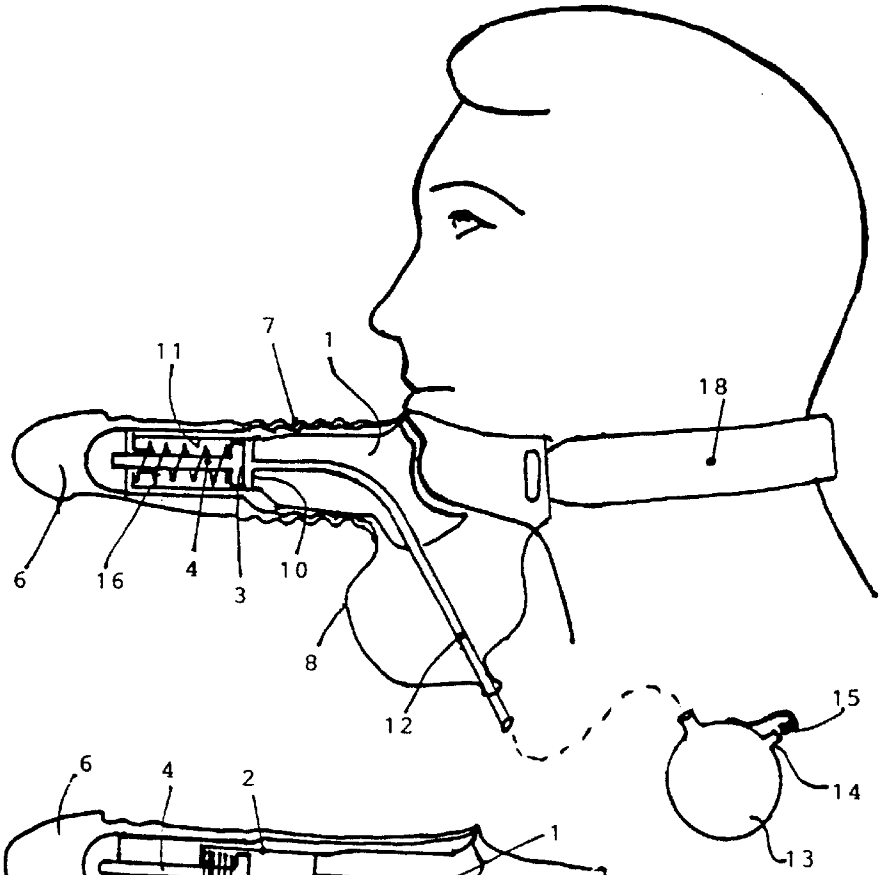
FIG. 1 shows a section through the thrust rod in the retracted position.

The device contains a seating support 1, to which is adjoined a pressure cylinder 2, in which is guided a piston 3 with a piston rod 4 fastened to it. A thrust cylinder 5 is fastened to the front end of the piston rod 4, and is furthermore guided on the outer surface of the pressure cylinder 2. The parts 1–5 form a core which is covered by an outer sheath 6. The outer sheath consists of soft latex, has the form of a penis, and is connected at the penis root to the seating support 1. An extension section 7 is located between this attachment point and the penis tip, and can assume a wave shape. A scrotum 8 of soft latex can be attached to the penis root.

Figure 2:
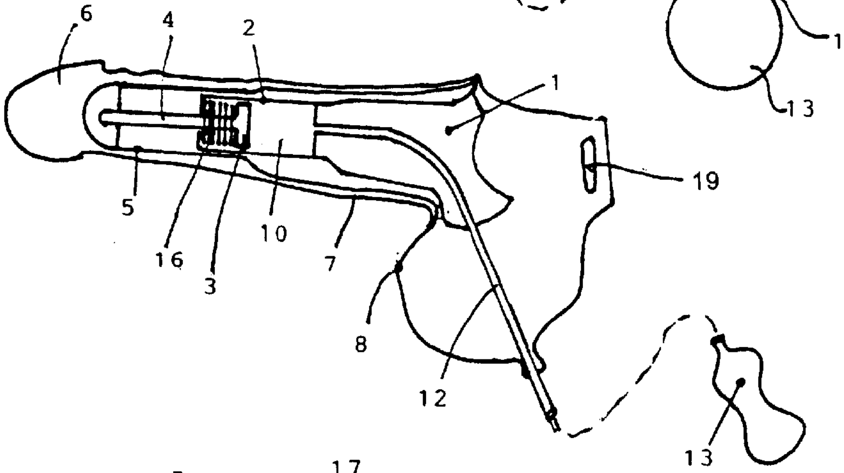
FIG. 2 shows a section in the extended position.
Figure 3:
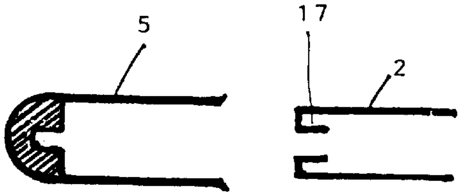
FIG. 3 shows two individual parts.

The piston 3 divides the pressure cylinder 2 into a pressure space 10 and a further space 11. The pressure space 10 is connected via a duct 12 to an air supply bellows 13, which has a mouthpiece 14 and a closure 15. The portions 10, 12 and 13 form communicating tubes, that is, air (or another fluid), which is forced out of the bellows 13, passes into the pressure space 10 and pushes the piston 3 against a restoring force. When the bellows 13 is released, the air (or the fluid) is forwarded out of the pressure space 10 and back into the bellows 13, due to the restoring force. The device can thus be actuated as a thrust rod by pressing and releasing the bellows 13: FIG. 1 illustrates the initial position, and FIG. 2 illustrates the extended position of the thrust rod.

The restoring force can be produced by a corresponding constitution of the outer sheath 6, in particular in the region 7; however, it is also possible to use here a coil spring 16 which extends between a collar 17 of the cylinder 2 and the piston 3, and which surrounds the piston rod 4.

The portion 8 has eyelets 17 to which a band 18 is joined in order, for example, to be fastened around the neck of a wearer, as shown in FIG. 1.

In a modification of the embodiment shown, the bellows 13 can also be installed in the portion 8.

The mouthpiece 14 with closure 15 makes it possible to suitably change the internal pressure of the device.

What is claimed is:

1. An artificial penis, comprising:

a support for said artificial penis at the body of a person, a cylinder having a cylinder wall enclosing a hollow, a front wall with a first opening in and a rear wall with a second opening in it, a piston carrying a piston rod and being guided within said hollow of said cylinder so as to define a first cylinder space and a second cylinder space, said piston rod being partly arranged in said first cylinder space and having a free end extending through said first opening in said front wall, said piston and said piston rod having an initial position in which said first cylinder space is at a maximum and said second cylinder space is at a minimum and an extended position in which said first cylinder space is at a minimum and said second cylinder space at a maximum, a pump adapted to supply a fluid under pressure when manually activated, said pump being connected to said second cylinder space through a pipe device and through said second opening in said rear wall of said cylinder so as to move said piston and said piston rod in an extending direction of said piston rod, a return device that moves said piston and said piston rod to said initial position, an enclosure having an outer shape of a penis and enclosing said cylinder and said piston rod end extending through said first opening in said front wall of said cylinder, said enclosure being fixed to said support and comprising extendable portions so that the enclosure has an initial position when said pump is released and an extended position when said pump is actuated.

2. The artificial penis set forth in claim 1, wherein said enclosure comprises a soft latex sheath member and a pusher member fixed to said free end of said piston rod, said pusher member, when driven by said piston rod, extending said enclosure in said extended position thereof.

3. The artificial penis set forth in claim 2, wherein said pusher member has the shape of a sleeve and is telescopically guided on said cylinder wall of said cylinder.

4. The artificial penis set forth in claim 1, wherein said return device comprises a coil spring arranged in said first cylinder space.

5. The artificial penis according to claim 1, wherein said pump comprises a bellows.

6. The artificial penis set forth in claim 1, wherein said support comprises an elastic band adapted to fasten said enclosure to said body of a person.

7. The artificial penis set forth in claim 1, wherein said fluid comprises air.

8. The artificial penis set forth in claim 5, wherein said bellows has a mouth piece for blowing air into said bellows and a shutter for closing said mouth piece.

9. The artificial penis set forth in claim 7, wherein said fluid comprises air and said bellows has a mouth piece for blowing air into said bellows and a shutter for closing said mouth piece.

* * * * *